US00PP37328P2

(12) United States Plant Patent
Lynd

(10) Patent No.: US PP37,328 P2
(45) Date of Patent: Mar. 17, 2026

(54) APPLE TREE NAMED 'MAIA-RZ'

(50) Latin Name: ***Malus* x *domestica***
Varietal Denomination: MAIA-RZ

(71) Applicant: Midwest Apple Improvement Association, Amherst, OH (US)

(72) Inventor: Andrew M. Lynd, Pataskala, OH (US)

(73) Assignee: Midwest Apple Improvement Association, Amherst, OH (US)

( * ) Notice: Subject to any disclaimer, the term of this patent is extended or adjusted under 35 U.S.C. 154(b) by 0 days.

(21) Appl. No.: 18/921,762

(22) Filed: Oct. 21, 2024

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875
See application file for complete search history.

*Primary Examiner* — Kent L Bell
(74) *Attorney, Agent, or Firm* — Weatherly IP Solutions, LLC; Karen P. Bechtold; James M. Weatherly

(57) ABSTRACT

A new apple tree particularly distinguished by fruit having a dark red color with a predominantly conical shape that fruit ripens 7 to 10 days later than the commercial variety 'Honeycrisp', is disclosed.

3 Drawing Sheets

Genus and species: *Malus* x *domestica*.
Variety denomination: 'MAIA-RZ'.

BACKGROUND OF THE NEW PLANT

The present invention comprises a new and distinct variety of apple tree, botanically known as *Malus* x *domestica* and hereinafter referred to by the variety name 'MAIA-RZ'. 'MAIA-RZ' originated from a population of seedlings from an open pollination conducted in 2003 of the commercial apple tree variety 'Honeycrisp' (U.S. Plant Pat. No. 7,197) and an unknown pollen parent. In 2005, seedlings from the 2003 cross were planted as one-year old trees in Newark, Ohio. Evaluations began in 2010, and a seedling variety was identified having desirable properties in 2011 and subsequently named 'MAIA-RZ'. 'MAIA-RZ' was asexually reproduced in 2014 in Newark, Ohio by vegetative cuttings from budwood which was graphed on 'G.41' rootstock (U.S. Plant Pat. No. 17,139).

The variety 'MAIA-RZ' is distinct from the female parent 'Honeycrisp' based on 'MAIA-RZ's stronger red coloration, with a darker and more complete shade of red, covering 80-90% of the fruit. 'MAIA-RZ' fruit ripens 7-10 days later than 'Honeycrisp', and the fruit shape is conical versus the oblate/roundly oblate shape of 'Honeycrisp'.

SUMMARY

The following are the most outstanding and distinguishing characteristics of this new variety when grown under normal horticultural practices in Newark, Ohio.

1. The fruit of 'MAIA-RZ' have a predominantly conical shape.
2. The fruit ripens 7-10 days later than the 'Honeycrisp'.
3. The fruit is darker red, with more complete coloring and more intense flavor profile than 'Honeycrisp' apple used in the open-pollination cross.

DESCRIPTION OF THE PHOTOGRAPHS

'MAIA-RZ' is illustrated by the accompanying photographs from September 2023 of plants grown in Pataskala, Ohio and Biglerville, Pennsylvania. The colors shown are as true as can be reasonably obtained by conventional photographic procedures.

DESCRIPTION OF THE NEW VARIETY

Figure 1:
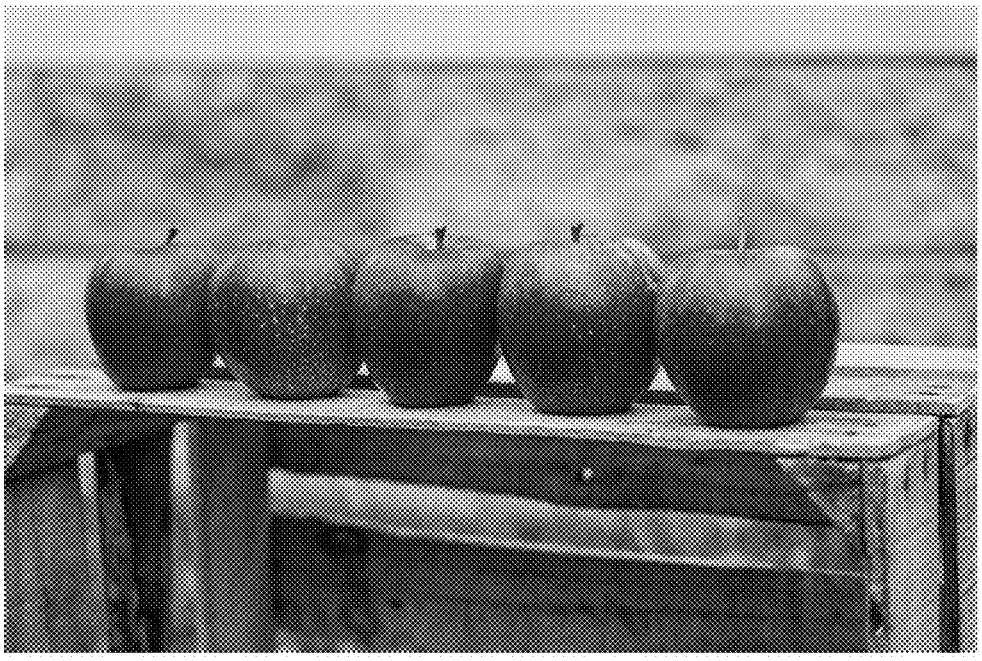
FIG. 1 shows fruit harvested from an orchard in Pataskala, Ohio showing the typical color and shape of the new 'MAIA-RZ' variety.
Figure 2:
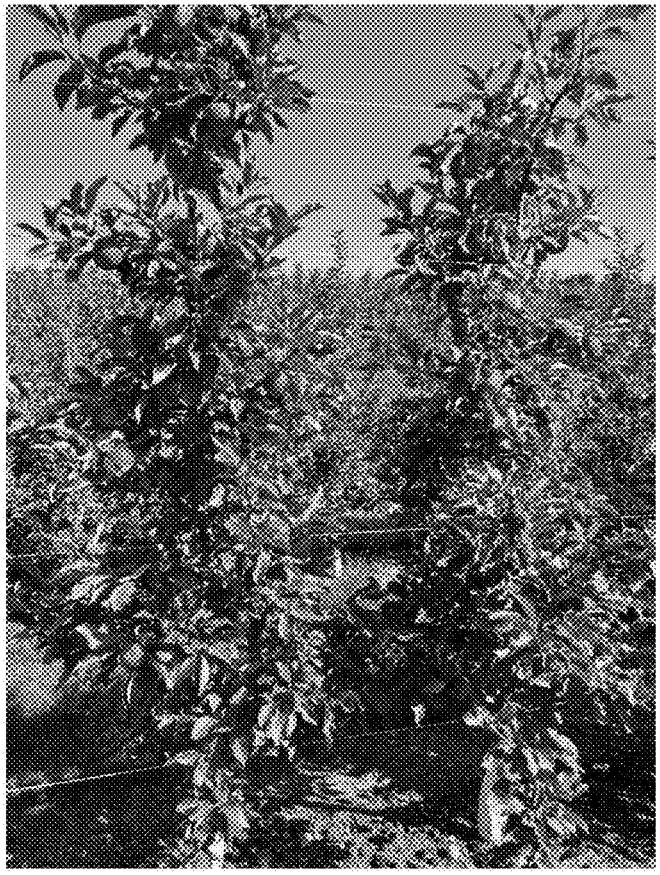
FIG. 2 shows the overall habit of two five-year-old 'MAIA-RZ' trees in Biglerville, Pennsylvania grown on a wire trellis.
Figure 3:
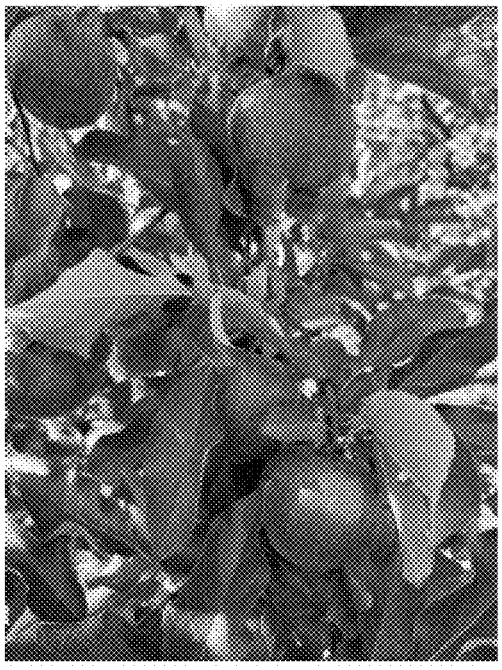
FIG. 3 shows a close-up view of the leaves and fruit on a five-year-old 'MAIA-RZ' tree in Biglerville, Pennsylvania.

The following detailed descriptions set forth the distinctive characteristics of 'MAIA-RZ'. The data which define these characteristics was collected in Biglerville, Pennsylvania in 2023. The age of 'MAIA-RZ' plants where relevant are provided below. All colour determinations were made using 2015 (2019 Reprint) Royal Horticultural Society (R.H.S.) Colour Chart.

Classification:
- *Family*.—Rosaceae.
- *Botanical*.—*Malus* x *domestica*.
- *Common name*.—Apple.
- *Variety name*.—'MAIA-RZ'.

Parentage:
- *Female parent*.—Commercial variety 'Honeycrisp' (U.S. Plant Pat. No. 7,197).
- *Male parent*.—Unknown.

General description:
- *Plant habit*.—Upright, trained to central leader.
- *Height and spread*.—10.0 feet to 12.0 feet high, 4.0 foot spread.
- *USDA hardiness zone*.—Zones 6a to 8a (2023 USDA Plant Hardiness Zone Map).

Trunk:
*Diameter.*—12.0 cm at 50.0 cm in height (5 years old).
*Bark color.*—RHS N200C (Light brownish grey) (5 years old).
*Lenticels.*—Density: 6 per square inch. Color: RHS N200A (Dark greyish yellowish brown). Shape: Oblong. Size: Length: 7.0 mm. Width: 1.0 mm.
*Description of dormant shoots* (*one year old*).—Pubescence: Heavy. Shoot size: Length: 30.0 cm to 45.0 cm. Width: 6.0 mm to 7.0 mm at base; 3.0 mm to 4.0 mm at tip. Anthocyanin: Absent. Thickness of shoot at center of middle internode: 4.8 mm. Bark color: RHS N199A (Moderate olive brown). Lenticel color: RHS 4D (Pale yellow green). Shoot angle: 43 degrees. Branch internode length: 28.0 mm.
*Vegetative buds.*—Length: 2.7 mm. Width: 1.3 mm. Shape: Narrow, pointed.
*Color of growing tip of shoot.*—RHS 199D (Dark greenish yellow).
*Pubescence of shoots tip.*—Present.

Foliage:
*Leaf shape.*—Elliptical.
*Leaf apex.*—Acuminate.
*Leaf base.*—Oblique.
*Leaf venation.*—Pinnate.
*Leaf margins.*—Serrulate.
*Leaf arrangement.*—Alternate.
*Leaf aspect.*—Whorl.
*Leaf size.*—Length: 11.0 mm. Width: 55.0 mm.
*Leaf internode length.*—28.0 mm.
*Leaf color* (*R.H.S.*).—Adaxial surface: 137A (Moderate olive green). Abaxial surface: 147C (Moderate yellow green). Leaf venation: 145C (Light yellow green).
*Leaf stipules.*—Width: 6.0 mm. Length: 1.0 mm. Color: RHS 145C.

Petioles:
*Length.*—42.0 mm.
*Width.*—1.9 mm.
*Color.*—RHS 145C.
*Petiole groove.*—Visible entire length on adaxial side on larger leaves.

Leaf buds:
*Arrangement.*—Alternate.
*Color.*—RHS N200A (Dark greyish yellowish brown).
*Size.*—Length: 2.7 mm. Width: 1.3 mm.
*Internode distance.*—1.0 cm to 2.0 cm.

Inflorescence description (flowers at popcorn stage):
*Pedicel size.*—Length: 15.8 mm. Width: 1.77 mm.
*Pedicel color.*—RHS 147B (Moderate yellow green).
*Bud size.*—Length: 11.2 mm. Width: 8.15 mm.
*Bud color before flower petals expand.*—RHS 64B and RHS 64C (Purplish red).

Inflorescence description (flowers at full bloom):
*Blooming period.*—Approximately 7 days, but varies with temperature.
*Presentation.*—Large, showy blossoms.
*Flower fragrance.*—Lightly aromatic.
*Flower quantity.*—5 per cluster.
*Corolla diameter.*—40.0 mm to 43.0 mm.
*Corolla depth.*—8.0 mm.

Calyx: Closed, medium with small sepals.

Sepals:
*Quantity per flower.*—5.
*Shape.*—Lanceolate.
*Margin.*—Smooth.
*Length.*—7.6 mm.
*Width.*—3.9 mm at base; 0.5 mm at tip.
*Color* (*R.H.S.*).—Lower surface: 145B (Light yellow green) at base; 143C at tips.
*Apex shape.*—Attenuate.
*Apex surface color.*—RHS 145A.

Petals:
*Quantity per flower.*—5.
*Shape.*—Rounded ovate.
*Apex.*—Rounded.
*Base.*—Notched.
*Margin.*—Smooth.
*Length.*—20.6 mm.
*Width.*—13.7 mm.
*Color.*—Upper surface (inside): RHS NN155D (White). Lower surface (outside): RHS NN155C (White).
*Veins.*—Visible at base, up to middle of petal.
*Surface texture.*—Soft.

Pedicels:
*Length.*—22.8 mm.
*Width.*—1.6 mm at center; 3.1 mm at base.
*Color.*—RHS 146D (Moderate yellow green).
*Texture.*—Pubescent.

Reproductive organs:
*Gynoecium.*—Stigma: Diameter: 1.79 mm. Color: RHS 150B (Brilliant yellow green). Above anthers: Absent. Style: Color: RHS 150A (Brilliant yellow green). Length: 3.0 mm. Width: 2.0 mm. Fused: Fused at base. Ovary: Color: RHS 144A (Strong yellow green). Length: 3.81 mm. Width: 2.16 mm.
*Androecium.*—Stamens: Quantity per flower: 14-17. Filament length: 5.0 mm to 9.0 mm. Filament width: 0.5 mm. Filament Color: RHS NN155C (White). Anther color: RHS 11A (Brilliant yellow).

Fertility:
*Fertile.*—Yes.
*Pollination requirements.*—Requires cross-pollination from diploid varieties with overlapping bloom timing.

Fruit description (5-year-old trees, freshly harvested fruit; Sep. 21, 2023 in Biglerville, Pennsylvania):
*Fruit.*—Shape: Conical. Size: Axial diameter: 70.0 mm. Traverse diameter: 75.0 mm, tapering to bottom diameter of 50.0 mm. Weight: Average 175 g. Use: Fresh market, desserts. Storage life: Excellent; stores well in refrigerated storage. Stalk: Length: 28.0 mm; extends significantly (approximately 10 mm to 12 mm) above shoulder of fruit. Thickness at middle: 2.5 mm. Thickness at attachment: 5.0 mm. Color: RHS 165B. Skin: Color: RHS 46A (Strong red). Ground color: RHS N34A (Moderate red) to RHS N34D (Moderate reddish orange). Stripe: Present. Stripe Color: RHS 14C. Lenticels: Typical number per fruit: approximately 650. Diameter: 1.3 mm. Color: RHS 145D (Light yellow green). Basin: shallow and wide, with mild to moderate ribbing. Width: 32.0 mm. Depth: 7.0 mm. Color: RHS N34D (Moderate reddish orange). Flesh: Color: RHS 11D (Pale yellow). Fragrance: Fresh, fruity. Texture: Firm, crisp. Flavor: Sweet, complex. Eating quality: Excellent. Core: Locules: 5 per fruit. Size: medium. Bundle area, size: visible, 961 $mm^2$. Seed cells: medium sized/tough walls. Seeds: Number per fruit:

10 seeds per fruit. Number per cell: 2. Color: RHS 200B (Greyish reddish brown). Size: Length: 8.6 mm. Width: 5.2 mm. Fruit production: Approximately 1,100 trees per acre, with a yield of approximately 0.9 bushels per tree and approximately 990 bushels per acre. Fruit Shipping Quality: Good. Fruit Storage Quality: Excellent.

Disease and pest resistance: No known resistance or susceptibility to common apple diseases and pests.

COMPARISON WITH KNOWN VARIETY

Table 1 below provides a comparison of 'MAIA-RZ' to a commercial 'Gala' apple (U.S. Plant Pat. No. 3,637).

TABLE 1

| Characteristic | 'Maia-RZ' | 'Gala' |
|---|---|---|
| Maturation time | 1 to 2 weeks later than the 'Gala' | 1 to 2 weeks earlier than 'MAIA-RZ' |
| Skin color | 80-90% darker, more complete red | Lighter and less red color |
| Striping | Present | Absent |

I claim:

1. A new and distinct variety of apple tree designated 'MAIA-RZ' as illustrated and described herein.

* * * * *